US006613938B2

(12) United States Patent
Zoeller et al.

(10) Patent No.: US 6,613,938 B2
(45) Date of Patent: Sep. 2, 2003

(54) METHOD FOR CARBONYLATION OF LOWER ALIPHATIC ALCOHOLS USING TIN PROMOTED PLATINUM CATALYST

(75) Inventors: Joseph Robert Zoeller, Kingsport, TN (US); Andy Hugh Singleton, Kingsport, TN (US); Gerald Charles Tustin, Kingsport, TN (US); Donald Lee Carver, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 109 days.

(21) Appl. No.: 09/884,815

(22) Filed: Jun. 19, 2001

(65) Prior Publication Data

US 2003/0018212 A1 Jan. 23, 2003

(51) Int. Cl.[7] .............................................. C07C 67/36
(52) U.S. Cl. ........................ 560/207; 560/232; 562/519; 562/520; 562/522
(58) Field of Search ................................ 560/232, 240, 560/207; 562/519, 520, 522; 260/488

(56) References Cited

U.S. PATENT DOCUMENTS

| | | |
|---|---|---|
| 3,689,533 A | 9/1972 | Schultz |
| 3,717,670 A | 2/1973 | Schultz |
| 3,772,380 A | 11/1973 | Paulik et al. |
| 4,417,077 A | 11/1983 | Drago et al. |
| 4,433,166 A | 2/1984 | Singleton et al. |
| 4,612,387 A | 9/1986 | Feitler |
| 4,776,987 A | 10/1988 | Luft et al. |
| 4,845,163 A | 7/1989 | Panster et al. |
| 4,918,218 A | 4/1990 | Mueller et al. |
| 5,185,462 A | 2/1993 | Evans et al. |
| 5,218,140 A | 6/1993 | Wegman |
| 5,237,097 A | 8/1993 | Smith et al. |
| 5,258,549 A | 11/1993 | Pimblett |
| 5,488,143 A | 1/1996 | Uhm et al. |

FOREIGN PATENT DOCUMENTS

| | | | | |
|---|---|---|---|---|
| DE | 198 52 547 | * | 5/2000 | ............ C01G/1/02 |
| EP | 0 120 631 A1 | | 10/1984 | |
| EP | 0 759 419 A1 | | 2/1997 | |
| FR | 1573130 | * | 7/1969 | |
| WO | WO 00/48979 A1 | | 8/2000 | |
| WO | WO 01/77059 A2 | | 10/2001 | |

OTHER PUBLICATIONS

Kohji omata, "Vapour–Phase Carbonylation of Methanol over Tin Catalyst Supported on Active Carbon", Chem. Lett., (1987), pp. 2397–2398.*

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 60, No. 8, (1988) p. 1315–1320, Great Britain.

H. Yagita, K. Omata, H. Tominaga and K. Fujimoto, "Vapor– phase Carbonylation of Methanol Over Lead on Active Carbon Catalyst", *Catalysis Letters*, 2 (1989) p. 145–148, Germany.

H. Yagita and K. Fujimoto, "Redox Cycle of Metal–on–Active Carbon Catalyst in the Vapor Phase Carbonylation of Methanol", *Journal of Molecular Catalyst*, 69 (1991) p. 191–197, Netherlands.

K. Fujimoto, S. Bischoff, K. Omata and H. Yagita, "Hydrogen Effects on Nickel–Catalyzed Vapor–Phase Methanol Carbonylation", *Journal of Catalysis*, 133 (1992) p. 370–382.

M. J. Howard, M. D. Jones, M. S. Roberts and S. A. Taylor, "$C_1$ to Acetyls: Catalysis and Process", *Catalysis Today*, 18 (1993) p. 325–354, Amsterdam.

T. Liu and S. Chiu, "Promoting Effect of Tin on Ni/C Catalyst for Methanol Carbonylation", *Ind. Eng. Chem. Res.*, 33 (1994) p. 488–492, USA.

A. Krzywicki and M. Marczewski, "Formation and Evolution of the Active Site for Methanol Carbonylation on Oxide Catalysts Containing $RhCl_3$", *Journal of Molecular Catalysis*, 6 (1979) p. 431–440, Netherlands.

K. Fujimoto, H. Mazaki, K. Omata and H. Tominaga, "Promotion Effect of Hydrogen on Vapor Phase Carbonylation of Methanol Over Nickel on Active Carbon Catalyst", *Chemistry Letters*, (1987) p. 895–898, Japan.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) p. 421–429, Netherlands.

Tuan–Chi Liu and Shwu–Jer Chiu, "Effect of Tin on NI/C Catalyst for Methanol Carbonylation", *Ind. Eng. Chem. Res.*, 1994, vol. 33, No. 3, pp. 488–492, American Chemcial Society.

Fabio B. Passos, Donato A. G. Aranda and Martin Schmal, "Characterization and Catalytic Activity of Bimetallic Pt–In/$Al_2O_3$ and Pt–Sn/$Al_2O_3$Catalysts", *J. Cat.*, 1998, 178, pp. 478–488, Academic Press.

M.J. Howard, M.D. Jones, M.S. Roberts and S.A. Taylor, "$C_1$ to acetyls: catalysis and process", *Cat. Today*, 1993, pp. 325–354, Elsevier Science Publishers, B.V. Amsterdam.

* cited by examiner

*Primary Examiner*—Paul J. Killos
(74) *Attorney, Agent, or Firm*—Michael Blake; Bernard J. Graves, Jr.

(57) ABSTRACT

A vapor-phase carbonylation method for producing esters and carboxylic acids from reactants comprising lower alkyl alcohols, lower alkyl alcohol generating compositions and mixtures thereof. The method includes contacting the reactants and carbon monoxide in a carbonylation zone of a carbonylation reactor under vapor-phase conditions with a catalyst having a catalytically effective amount of platinum and tin associated with a solid carrier material.

19 Claims, No Drawings

METHOD FOR CARBONYLATION OF LOWER ALIPHATIC ALCOHOLS USING TIN PROMOTED PLATINUM CATALYST

BACKGROUND OF THE INVENTION

The present invention relates to a method for the vapor-phase carbonylation of lower alkyl alcohols, ether and ester derivatives of the alcohols, and mixtures thereof to produce esters and carboxylic acids. Particularly, the present invention relates to a method for the vapor-phase carbonylation of methanol to produce acetic acid and methyl acetate using a solid catalyst having platinum and tin associated with a solid support material.

Lower carboxylic acids and esters such as acetic acid and methyl acetate have been known as industrial chemicals for many years. Acetic acid is used in the manufacture of a variety of intermediary and end-products. For example, an important derivative is vinyl acetate that can be used as a monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters, as illustrated in equations 1–3 below:

$$ROH + CO \rightarrow RCOOH \quad (1)$$

$$2ROH + CO \rightarrow RCOOR + water \quad (2)$$

$$ROR' + CO \rightarrow RCOOR \quad (3)$$

Carbonylation of methanol is a well-known reaction and is typically carried out in the liquid phase with a catalyst. A thorough review of these commercial processes and other approaches to accomplishing the formation of acetyl from a single carbon source is described by Howard et al. in *Catalysis Today*, 18, 325–354 (1993). Generally, the liquid phase carbonylation reactions for the preparation of acetic acid using methanol are performed using homogeneous catalyst systems comprising a Group VIII metal and a halogen component such as iodine or bromine or an iodine or bromine-containing compound such as hydrogen iodide, hydrogen bromide, methyl iodide, or methyl bromide. Rhodium is the most common Group VIII metal catalyst and methyl iodide is the most common promoter. These reactions are conducted in the presence of water to prevent precipitation of the catalyst.

These recently developed processes represent a distinct improvement over the classic carbonylation processes wherein such feed materials have been previously carbonylated in the presence of such catalyst systems as phosphoric acid, phosphates, activated carbon, heavy metal salts and metal carbonyls such as cobalt carbonyl, iron carbonyl and nickel carbonyl. All of these previously known processes require the use of extremely high partial pressures of carbon monoxide. They also have the disadvantage of requiring higher catalyst concentrations, longer reaction times, and higher temperatures to obtain substantial reaction and conversion rates. This results in needing larger and more costly processing equipment and higher manufacturing costs.

A disadvantage of a homogeneous phase carbonylation process is that additional steps are necessary for separating the products from the catalyst solutions, and there are always handling losses of the catalyst. Losses of the metal in the catalyst can be attributed to several factors, such as the plating-out of the active metal onto piping and process equipment thereby rendering the metal inactive for carbonylation purposes and losses due to incomplete separation of the catalyst from the products. These losses of the metal component are costly because the metals themselves are very expensive.

Schultz, in U.S. Pat. No. 3,689,533, discloses using a supported rhodium heterogeneous catalyst for the carbonylation of alcohols to form carboxylic acids in a vapor-phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772,380, describe the use of iridium on an inert support as a catalyst in the vapor phase, halogen-promoted, heterogeneous alcohol carbonylation process.

European Patent Application EP 0 759 419 A1 pertains to a process for the carbonylation of an alcohol and/or a reactive derivative thereof. EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium, and nickel, and an optional metal promoter on a carbon support. The optional metal promoter may be iron, nickel, lithium and cobalt. The conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst and costly replacement of the active catalyst component.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3, 421–429 (1988). Gelin et al., in *Pure & Appl. Chem.*, Vol. 60, No. 8, 1315–1320 (1988), provide examples of the use of rhodium or iridium contained in zeolite as catalysts for the vapor phase carbonylation of methanol in the presence of halide promoter. Krzywicki et al., in *Journal of Molecular*

Catalysis, 6, 431–440 (1979), describe the use of silica, alumina, silica-alumina and titanium dioxide as supports for rhodium in the halide-promoted vapor phase carbonylation of methanol, but these supports are generally not as efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component. Typically, these catalysts are unstable at elevated temperatures making them poorly suited to vapor phase processes.

Nickel on activated carbon has been studied as a heterogeneous catalyst for the halide-promoted vapor phase carbonylation of methanol. Relevant references to the nickel-on-carbon catalyst systems are provided by Fujimoto et al. in *Chemistry Letters* 895–898, (1987). Moreover, Fujimoto et al. in *Journal of Catalysis*, 133, 370–382 (1992) observed increased rates when hydrogen is added to the feed mixture. Liu et al., in *Ind. Eng. Chem. Res.*, 33 488–492, (1994), report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2, 145–148 (1989) to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

Yagita and Fujimoto in *Journal of Molecular Catalysis*, 69, 191–197 (1991) examined the role of activated carbon in a metal supported catalyst and observed that the carbonylation activities of Group VIII metals supported on activated carbon are ordered by the affinities between the metal and the halogen.

Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140, describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometallate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase.

In accordance with the present invention, a method for the heterogeneous vapor-phase carbonylation of reactants comprising lower alkyl alcohols, ether and ester derivatives of the alcohols, and ester-alcohols mixtures is provided using a catalyst that includes a catalytically effective amount of platinum and tin associated with a solid support material which, desirably, is inert to the carbonylation reaction.

SUMMARY OF THE INVENTION

Briefly, the present invention is a method for the vapor-phase carbonylation of reactants comprising lower alkyl alcohols, lower alkyl alcohol generating compositions such as ether and ester derivatives of the alcohols, and mixtures thereof for producing esters and carboxylic acids. The method includes contacting the reactants under vapor-phase carbonylation reaction conditions with a heterogeneous catalyst having a catalytically effective amount of platinum and/or platinum salt and tin and/or tin salt associated with a solid support material. In a preferred embodiment, the method also includes contacting the reactants, in the presence of the solid catalyst, with a vaporous halide promoter. As used herein the term "associated with" means any manner for incorporating or associating the platinum metal and/or its salt and the tin metal and/or its salt on or in the solid support material. Non-limiting examples in which the platinum and tin metals or their respective salts may be associated with the solid support include impregnating, immersing, spraying and coating the support with a solution containing platinum and with a solution containing tin sequentially or impregnating, immersing, spraying and coating the support with a solution containing a mixture of platinum and tin.

It is an object of the invention to provide a method for the carbonylation of lower alkyl alcohols, ethers, and ester-alcohol mixtures to produce esters and carboxylic acids. More particularly, it is an object of the present invention to provide a vapor-phase carbonylation method for the production of acetic acid, methyl acetate and mixtures thereof from a lower alkyl alcohol and preferably, methanol.

It is another object of the invention to provide a process in which the catalyst is maintained in a solid phase to reduce or eliminate the handling losses of the catalyst.

It is another object of the invention to provide a vapor phase carbonylation process for the production of acetic acid and methyl acetate which utilizes a more stable catalyst and reduces the need for catalyst recovery and recycle as well as solvent recovery.

These and other objects and advantages of the invention will become apparent to those skilled in the art from the accompanying detailed description.

DETAILED DESCRIPTION OF THE INVENTION

In accordance with the invention, a vapor-phase carbonylation method is provided for the continuous production of carboxylic acids and esters by contacting lower alkyl alcohols, lower alkyl alcohol generating compositions such as ether and/or ester derivatives of the alcohol, and mixtures thereof, and carbon monoxide with a solid supported catalyst. The catalyst includes an effective amount of platinum and/or platinum salt and tin and/or tin salt associated with a solid support material which, desirably, is inert to the carbonylation reaction. In a preferred embodiment of the present process, the reactant is fed in conjunction with a vaporous halide promoter. In a preferred embodiment, the present invention provides for the vapor-phase carbonylation of methanol for the continuous production of acetic acid, methyl acetate or mixtures thereof.

The process of this invention is operated in the vapor phase and, therefore, is practiced at temperatures above the dew point of the reactants and product mixture, i.e., the temperature at which condensation occurs. However, since the dew point is a complex function of dilution (particularly with respect to non-condensable gases such as unreacted carbon monoxide, hydrogen, or inert diluent gas), reactant and product composition, and pressure, the process may still be operated over a wide range of temperatures, provided the temperature exceeds the dew point of the reactants and products. In practice, this generally dictates a temperature range of about 100° C. to 500° C., with temperatures in the range of 100° C. to 325° C. being preferred and temperature of about 150° C. to 275° C. being particularly useful. Advantageously, operating in the vapor phase eliminates catalyst dissolution, i.e., metal leaching from the catalyst support, which occurs in the known heterogeneous processes operating in the presence of liquid compounds.

As with temperature, the useful pressure range for the vapor phase carbonylation is limited by the dew point of the product mixture. Provided that the reaction is operated at a temperature sufficient to prevent liquefaction of the reactants and products, a wide range of pressures may be used, e.g., pressures in the range of about 0.1 to 100 bars absolute. The process preferably is carried out at a pressure in the range of about 1 to 50 bars absolute, most preferably, about 3 to 30 bar absolute (bara).

Suitable feedstock, i.e., reactants, for carbonylation using the catalyst of the present invention include lower alkyl alcohols, lower alkyl alcohol generating compositions such as ether and ester derivatives of the alcohols, and mixtures thereof. Non-limiting examples of reactants include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is preferably used in the process and is normally fed as methanol, it can be supplied in the form of a combination of materials which generate methanol. Examples of such combination of materials include (i) methyl acetate and water and (ii) dimethyl ether and water. In the operation of the process, both methyl acetate and dimethyl ether are formed within the reactor and, unless methyl acetate is the desired product, they are recycled with water to the reactor where they are later consumed to form acetic acid.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the methyl ester, methyl acetate, is the desired product, no water should be added to the carbonylation process and dimethyl ether becomes the preferred feedstock. Further, when methanol is used as the feedstock in the preparation of methyl acetate, it is necessary to remove water. However, the primary utility of the process of the present invention is in the manufacture of acetic acid.

In the practice of a vapor-phase carbonylation process, the reactant, in the vapor phase, is passed through or over the solid supported platinum and tin catalyst and preferably the reactant is fed in conjunction with a vaporous halide promoter.

In preparing the solid supported catalyst, the form of platinum used generally is not critical. The solid supported component of the catalyst may be prepared from a wide variety of platinum containing compounds. For example, the platinum compound can be in the form of a salt of a mineral acid halide, such as chloroplatinic acid; trivalent nitrogen compounds such as dichlorodiammine platinum; organic compounds of trivalent phosphorous, such as dichlorobis (triphenylphosphine) platinum; olefins, such as dichloro(1, 5-cyclooctadiene) platinum; nitriles, such as dichlorobis (benzonitrile) platinum and oxides of platinum may be used if dissolved in the appropriate medium either alone or in combination. The preferred sources of platinum is one of it chlorides, such as any of the various salts of hexachloroplatinate(IV) or a solution of platinum dichloride in either aqueous HCl or aqueous ammonia.

The amount of platinum, as metal, on the support can vary from about 0.01 weight percent to about 10 weight percent, with from about 0.1 weight percent to about 2 weight percent platinum being preferred, wherein the weight percent is based on the total weight of the solid catalyst.

Likewise, the form of tin used in preparing the solid supported catalyst is not critical and may include a wide variety of tin containing compounds. For example, suitable tin compounds which may be associated with the solid support material include tin halides such as tin (II) chloride; alkyl carboxylate salts and aryl carboxylate salts wherein the alkyl group has from 1 to 10 carbon atoms and the aryl group has from 6 to 24 carbon atoms wherein at least one of the carbon atoms is bound to the tin moiety, tin oxides such as tin (II) oxalate, and mixtures of such tin containing compounds. The preferred sources of tin are tin (II) chloride, preferably dissolved in aqueous HCl, and tin (II) oxalate due to their availability, cost, lower toxicity, and high solubility in water (the preferred solvent medium).

The content of tin, as metal, on the support can vary over a wide range, for example from about 0.01 to 10 weight percent tin based on the total weight of the solid supported catalyst. However, the preferred amount of tin in the catalyst is from about 0.1 to 5 weight percent of tin based on the total weight of the solid supported catalyst.

The solid support useful for acting as a carrier for the platinum and tin consists of a porous solid of such size that it can be employed in fixed or fluidized bed reactors. Typical support materials have a size of from about 400 mesh per inch to about ½ inch. Preferably, the support is carbon, including activated carbon, having a high surface area. Activated carbon is well known in the art and may be derived from coal or peat having a density of from about 0.03 grams/cubic centimeter (g/cm$^3$) to about 2.25 g/cm$^3$. The carbon can have a surface area of from about 200 square meters/gram (m$^2$/g) to about 1200 m$^2$/g. Other solid support materials which may be used in accordance with the present invention include pumice, alumina, silica, silica-alumina, magnesia, diatomaceous earth, bauxite, titania, zirconia, clays, magnesium silicate, silicon carbide, zeolites, and ceramics. The shape of the solid support is not particularly important and can be regular or irregular and include extrudates, rods, balls, broken pieces and the like disposed within the reactor.

The platinum and tin can be associated with the solid support by solubilizing the metals, or their respective salts, in a suitable solvent and contacting the solubilized platinum and tin with the solid support material. The solvent is then evaporated so that at least a portion of the platinum and tin is associated with the solid support. Drying temperatures can range from about 100° C. to about 600° C. for a period greater than about one second. One skilled in the art will understand that the drying time is dependent upon the temperature, humidity, and solvent. Generally, lower temperatures require longer heating periods to effectively evaporate the solvent from the solid support. The method of preparing the solid component of the catalyst optionally further includes the step of heating the solid supported platinum and tin in a stream of inert gas. Non-limiting examples of suitable inert gases include nitrogen, argon and helium.

Alternatively the platinum and tin can be associated with the solid support by sequentially associating each metal with a support material. For example, platinum or a platinum containing salt would be solubilized using a suitable solvent. The dissolved metal solution would then be contacted with the support material. Afterwards, the solvent is evaporated so that at least a portion of the platinum is associated with the solid support material. Next, tin or a tin containing salt would be associated with the support material following a similar procedure as described for associating the platinum with the solid carrier. Thus, one will understand that multiple layers of the respective platinum and tin metals or metal containing compounds can be associated with the support by merely following multiple steps of the procedure described above.

In a preferred embodiment, the method further includes contacting the reactants, in the presence of the solid catalyst, with a vaporous halide promoter selected from chlorine, bromine and iodine compounds. Preferably, the vaporous halide is selected from bromine and iodine compounds that are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide, ethyl iodide, 1-iodopropane, 2-iodobutane, 1-iodobutane, methyl bromide, ethyl bromide, benzyl iodide and mixtures thereof. Desirably, the halide is a hydrogen halide or an alkyl halide having up to 6 carbon atoms. Non-limiting examples of preferred halides include hydrogen iodide, methyl iodide, hydrogen bromide, methyl bromide and mixtures thereof The halide may also be a molecular halide such as $I_2$, $Br_2$, or $Cl_2$.

The molar ratio of methanol or methanol equivalents to halide present to produce an effective carbonylation ranges from about 1:1 to 10,000:1, with the preferred range being from about 5:1 to about 1000:1.

In a preferred aspect of the invention, the vapor-phase carbonylation method of the present invention may be used for making acetic acid, methyl acetate or a mixture thereof The process includes the steps of contacting a gaseous mixture comprising methanol and carbon monoxide with a solid supported catalyst in a carbonylation zone and under carbonylation conditions and recovering a gaseous product from the carbonylation zone. The catalyst system includes a solid-phase component comprising platinum and tin deposited on an activated carbon support and a vaporous component comprising at least one of the halide promoters described above.

The carbon monoxide may be fed to the carbonylation zone either as purified carbon monoxide or as a mixture of hydrogen and carbon monoxide. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels may be useful.

The present invention is illustrated in greater detail by the specific examples present below. It is to be understood that these examples are illustrative embodiments and are not intended to be limiting of the invention, but rather are to be construed broadly within the scope and content of the appended claims.

EXAMPLES

Catalyst 1

In preparation the catalyst, 579 mg of dihydrogen hexachloroplatinate having an assay of 39.23% (1.17 mmol of Pt) was dissolved in 30 mL of distilled water. This solution was added to 20.0 grams of 12×40 mesh activated carbon granules contained in an evaporating dish. The activated carbon granules had a BET surface area in excess of 800 m$^2$/g. This mixture was heated using a steam bath and continuously stirred until the support granules became free flowing. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

To the catalyst prepared above was added a solution having 0.263 grams (1.17 mmol) of tin (II) chloride dihydrate dissolved in a mixture of 10 mL of 11.6 M HCl and 20 mL of distilled water. The catalyst mixture was heated again using the steam bath and continuously stirring until the granules became free flowing. The impregnated catalyst was then transferred to a quartz tube measuring 106 cm long by 25 mm outer diameter. The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

The solid supported catalyst in accordance with the present invention, (Catalyst I) contained 1.09% Pt, 0.66% Sn, and had a density of 0.57 g per mL.

Comparative Catalyst Example I

In preparing a comparative catalyst containing only platinum as the active metal, 569 mg of dihydrogen hexachloroplatinate having a Pt assay of 40%, (1.17 mmol of Pt) was dissolved in 30 mL of distilled water. This solution was added to 20.0 g of 12×40 mesh activated carbon granules contained in an evaporating dish. The activated carbon granules had a BET surface area in excess of 800 m$^2$/g. This mixture was heated using a steam bath and continuously stirred until the support granules became free flowing. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

The catalyst (Comparative Catalyst C-I) contained 1.10% Pt and had a density of 0.57 g per mL.

Comparative Catalyst Example II

A second comparative catalyst was prepared by dissolving 0.29 grams of nickelous acetate tetrahydrate (1.17 mmol) and 0.263 grams (1.17 mmol) of tin (II) chloride dihydrate in a solution consisting of 20 mL of distilled water and 10 mL of 11.6 M HCl. The solution was then added to 20.0 g of 12×40 mesh activated carbon granules contained in an evaporating dish. The activated carbon granules had a BET surface area in excess of 800 m$^2$/g. The impregnated catalyst was then transferred to a quartz tube measuring 106 cm long by 25 mm outer diameter. The quartz tube was thereafter placed in a three-element electric tube furnace so that the mixture was located in the approximate center of the 61 cm long heated zone of the furnace. Nitrogen was continuously passed through the catalyst bed at a rate of 100 standard cubic centimeters per minute. The tube was heated from ambient temperature to 300° C. over a 2 hour period, held at 300° C. for 2 hours and then allowed to cool back to ambient temperature.

The catalyst (Comparative Catalyst C-II) contained 0.33% Ni, 0.67% Sn, and had a density of 0.57 g per mL.

Comparative Catalyst Example III

A third comparative catalyst was prepared by dissolving 0.207 grams (1.17 mmol) of palladium chloride in 10 mL of 11.6 M HCl. In a separate vessel, 0.263 grams of tin (II) chloride dihydrate were dissolved in 10 mL of 11.6 M HCl. Both solutions were combined and mixed until uniform and the solution of dissolved palladium and tin was diluted with 10 mL of distilled water. The solution was then added to 20.0 g of 12×40 mesh activated carbon granules contained in an evaporating dish. The activated carbon granules had a BET surface area in excess of 800 m$^2$/g. The impregnated activated carbon granules were then dried using the procedure described above.

The catalyst (Comparative Catalyst C-III) contained 0.61% Pd, 0.68% Sn, and had a density of 0.57 g per mL.

Comparative Catalyst Example IV

A fourth comparative catalyst was prepared using the procedure described above to prepare the platinum catalyst in Comparative Catalyst Example I, except 418 mg (1.17 mmol) of iridium trichloride hydrate were used in place of the dihydrogen hexachloroplatinate. The catalyst (Comparative Catalyst C-IV) contained 1.10% Ir.

Carbonylation of Methanol

The reactor system consisted of a 800 to 950 mm (31.5 and 37 inch) section of 6.35 mm (¼ inch) diameter tubing constructed of Hastelloy C alloy. The upper portion of the tube constituted the preheat and reaction (carbonylation) zones. These zones were assembled by inserting a quartz wool pad 410 mm from the top of the reactor to act as support for the catalyst, followed sequentially by: (1) a 0.7 g bed of fine quartz chips (840 microns); (2) 0.5 g of one of the catalysts prepared as described in the preceding examples; and (3) an additional 6 g of fine quartz chips. The top of the tube was attached to an inlet manifold for introducing liquid and gaseous feeds.

The six grams of fine quartz chips acted as a heat exchange surface to vaporize the liquid feeds. Care was taken not to allow any of the liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using a vortex cooler operating at 0–5° C. The product reservoir was a tank placed downstream from the reactor system. The pressure was maintained using a modified Research control valve on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cc/min and the carbon monoxide flow rate was set at 100 cc/min. The reactor section was maintained under these conditions for 1 hour or until the temperature and pressure had stabilized, whichever was longer. The high pressure liquid chromatography pump was then started, feeding a mixture consisting of 70 weight percent methanol and 30 weight percent methyl iodide at a rate of 10–12 g per hour. Samples of the liquid product were collected and analyzed periodically using gas chromatographic techniques.

Carbonylation Example 1

The composition and weight of the samples taken periodically during the procedure described above in which Catalyst I was used are set forth in Table I. "Time" is the total time of carbonylation (in hours) commencing with the feeding of the methanol until a particular sample was taken. In the tables "MeI" is the weight percentage of methyl iodide present in the sample, "MeOAc" is the weight percentage of methyl acetate present in the sample, "MeOH" is the weight percentage of methanol present is the sample and "HOAc" is the weight percentage of acetic acid present in the sample. The weight of each sample is given in grams.

TABLE I

| Sample Number | Expired Time (h) | MeI | MeOAc | MeOH (Wt. %) | HOAc | Sample Weight (g) |
|---|---|---|---|---|---|---|
| 1 | 3.00 | 15.01 | 6.25 | 72.06 | 0.1 | 45.9 |
| 2 | 5.00 | 14.83 | 6.12 | 70.43 | 0.1 | 29.6 |
| 3 | 10.50 | 16.55 | 16.31 | 58.29 | 0.46 | 72.1 |
| 4 | 12.50 | 17.12 | 16.95 | 60.78 | 0.48 | 28.9 |
| 5 | 18.00 | 16.64 | 16.5 | 58.98 | 0.48 | 81.5 |
| 6 | 20.00 | 13.62 | 39.28 | 15.47 | 15.76 | 28.7 |
| 7 | 22.00 | 13.42 | 39.7 | 15.82 | 16.19 | 29 |
| 8 | 24.00 | 13.57 | 39.63 | 15.78 | 16.12 | 28.5 |
| 9 | 26.00 | 15.1 | 39.23 | 18.91 | 12.06 | 28.9 |
| 10 | 29.00 | 15.21 | 40.19 | 18.53 | 11.4 | 29.1 |
| 11 | 34.00 | 16 | 38.72 | 13.03 | 17.44 | 80.1 |
| 12 | 36.50 | 15.86 | 39.26 | 13.24 | 17.7 | 24.1 |
| 13 | 42.00 | 15.98 | 38.47 | 13.06 | 17.56 | 81.5 |
| 14 | 44.00 | 15.59 | 39.49 | 10.26 | 20.55 | 24.8 |
| 15 | 46.00 | 15.69 | 39.51 | 10.27 | 20.55 | 24.5 |

The rate of acetyl production based on the preceding experiment utilizing Catalyst I is set forth in Table II wherein Sample Number and Time values correspond to those of Table I, "Acetyl Produced" is the amount (millimoles) of methyl acetate and acetic acid produced during each increment of Time calculated from the formula:

(Sample Weight)×10×((weight % of MeOAc)/74)+((weight % of AcOH)/60)

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is:

((Acetyl Produced)/(0.5×Time Increment))×0.57 wherein 0.5 is the grams of catalyst used and 0.57 is the density of the catalyst in g/mL.

TABLE II

| Sample Number | Expired Time (h) | Acetyl Produced (mmol) | Rate (mol/L-h) |
|---|---|---|---|
| 1 | 3.00 | 39.5 | 15.0 |
| 2 | 5.00 | 25.0 | 14.2 |
| 3 | 10.50 | 164.4 | 34.1 |
| 4 | 12.50 | 68.5 | 39.0 |
| 5 | 18.00 | 188.2 | 39.0 |
| 6 | 20.00 | 227.7 | 129.8 |
| 7 | 22.00 | 233.8 | 133.3 |
| 8 | 24.00 | 229.2 | 130.6 |
| 9 | 26.00 | 211.3 | 120.4 |
| 10 | 29.00 | 213.3 | 81.1 |
| 11 | 34.00 | 651.9 | 148.6 |
| 12 | 36.50 | 199.0 | 90.7 |
| 13 | 42.00 | 662.2 | 137.3 |
| 14 | 44.00 | 217.3 | 123.9 |
| 15 | 46.00 | 214.7 | 122.4 |

Over the 46 hours of testing, the catalyst produced 3.55 moles of acetyl. This represents a rate of 154 moles of acetyl/kg$_{cat}$-h or, represented as an hourly space velocity, 88 mol of acetyl/L$_{cat}$-h.

Comparative Carbonylation Examples

Comparative Catalysts C-I-C-IV, were utilized in the carbonylation of methanol according to the above-described procedure. The Production Rate, expressed in terms of moles of Acetyl Produced per kilogram of catalyst per hour and moles per liter of catalyst volume per hour, for each of Catalyst I and Comparative Catalysts C-I-C-IV, are shown in Table III. As can be seen from Table III, the catalyst in accordance with the present invention is significantly more active than a catalyst using Pt as the sole active metal. Further, when compared to tin promoted catalysts for the other members of the triad, platinum is far superior to either nickel or palladium. Comparative Example C-4 shows that carbonylation rates using the catalyst of the present invention are superior to those obtained using iridium alone on an activated carbon support.

TABLE III

| Carbonylation | | Production Rate | |
|---|---|---|---|
| Example | Catalyst | in moles/kg$_{cat}$-h | in moles/L$_{cat}$-h |
| 1 | I (Pt—Sn) | 154 | 88 |
| C-1 | C-I (Pt) | 89 | 45 |
| C-2 | C-II (Ni—Sn) | 6 | 3 |
| C-3 | C-III (Pd—Sn) | 19 | 11 |
| C-4 | C-IV (Ir) | 93 | 53 |

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

We claim:

1. A vapor-phase carbonylation method for producing esters and carboxylic acids from reactants comprising lower alkyl alcohols, lower alkyl alcohol generating compositions, and mixtures thereof, said method comprising contacting the reactants and carbon monoxide with a catalyst in a carbonylation zone of a carbonylation reactor under vapor-phase conditions and wherein said catalyst consists essentially of a catalytically effective amount of platinum and tin associated with a solid carrier material.

2. The method of claim 1 wherein said reactants are selected from the group consisting of lower alkyl alcohols having from 1 to 10 carbon atoms, alkane polyols having 2 to 6 carbon atoms, alkyl alkylene polyethers having 3 to 20 carbon atoms and alkoxyalkanols having from 3 to 10 carbon atoms and mixtures thereof.

3. The method of claim 1 wherein said reactant is methanol.

4. The method of claim 1 wherein said reactant is dimethyl ether.

5. The method of claim 1 wherein esters and carboxylic acids produced from said vapor phase include acetic acid, methyl acetate and mixtures thereof.

6. The method of claim 1 further comprising contacting said reactants in said carbonylation zone with a vaporous halide compound selected from the group consisting of hydrogen iodide, hydriodic acid; methyl iodide, ethyl iodide, 1-iodopropane, 2-iodobutane, 1-iodobutane, benzyl iodide, hydrogen bromide, methyl bromide and mixtures thereof.

7. The method of claim 6 wherein said halide is selected from the group consisting of iodine, hydrogen iodide, methyl iodide, bromine, hydrogen bromide, methyl bromide and mixtures thereof.

8. The method of claim 1 wherein said carbonylation zone is maintained at a temperature of about 100° C. to 350° C. and a pressure of about 1 to 50 bar absolute.

9. The method of claim 1 wherein said solid carrier material is activated carbon.

10. The method of claim 1 wherein includes from about 0.1 weight percent to about 10 weight percent each of said platinum and tin.

11. The method of claim 1 wherein said catalyst includes from about 0.1 weight percent to about 2 weight percent each of said platinum and tin.

12. A vapor-phase carbonylation method for producing acetic acid, methyl acetate or a mixture thereof comprising the steps of:
   a. under vapor-phase carbonylation conditions of temperature and pressure, contacting a gaseous mixture comprising methanol, carbon monoxide, and a halide with a solid catalyst in a carbonylation zone of a carbonylation reactor wherein said solid catalyst consists essentially of from about 0.01 to about 10 weight % of platinum and from about 0.01 to about 10 weight % tin associated with a solid carrier material and wherein the weight % of the platinum and tin are based on the total weight of the catalyst; and
   b. recovering acetic acid, methyl acetate or a mixture thereof from the gaseous product.

13. The method of claim 12 wherein said halide is selected from the group consisting of hydrogen iodide, hydriodic acid; methyl iodide, ethyl iodide, 1-iodopropane, 2-iodobutane, 1-iodobutane, benzyl iodide, hydrogen bromide, methyl bromide and mixtures thereof.

14. The method of claim 13 wherein said halide is selected from the group consisting of iodine, hydrogen iodide, methyl iodide, bromine, hydrogen bromide, methyl bromide and mixtures thereof.

15. The method of claim 12 wherein said carbonylation zone is maintained at a temperature of about 100° C. to 350° C. and a pressure of about 1 to 50 bar absolute.

16. The method of claim 12 wherein said catalyst includes from about 0.1 weight percent to about 2 weight percent each of said platinum and tin.

17. A vapor-phase carbonylation method for producing acetic acid, methyl acetate or a mixture thereof comprising the steps of:
   a. under vapor-phase carbonylation conditions of temperature and pressure, contacting a gaseous mixture comprising methanol, carbon monoxide, and a halide with a solid catalyst in a carbonylation zone of a carbonylation reactor wherein said solid catalyst consists essentially of from about 0.1 weight % to about 2 weight % of platinum and from about 0.1 weight % to about 2 weight % tin associated with a solid carrier material and wherein the weight % of the platinum and tin are based on the total weight of the catalyst; and product.
   b. recovering acetic acid, methyl acetate or a mixture thereof from the gaseous product.

18. The method of claim 17 wherein said halide is selected from the group consisting of hydrogen iodide, hydriodic acid; methyl iodide, ethyl iodide, 1-iodopropane, 2-iodobutane, 1-iodobutane, benzyl iodide, hydrogen bromide, methyl bromide and mixtures thereof.

19. The method of claim 12 wherein said carbonylation zone is maintained at a temperature of about 100° C. to 350° C. and a pressure of about 1 to 50 bar absolute.

* * * * *